United States Patent [19]

Cormier et al.

[11] 4,283,262
[45] Aug. 11, 1981

[54] ANALYSIS SYSTEM

[75] Inventors: Alan D. Cormier, Newburyport; Milo E. Webster, Braintree; John D. Czaban, Bradford; Neil D. Silverman, Framingham; Lynn W. Noble, Acton, all of Mass.

[73] Assignee: Instrumentation Laboratory Inc., Lexington, MA

[21] Appl. No.: 165,051

[22] Filed: Jul. 1, 1980

[51] Int. Cl.³ .................. G01N 27/28; G01N 35/08
[52] U.S. Cl. .................................. 204/195 M; 73/53; 73/61 R; 73/61.1 R; 204/195 R; 204/195 B; 422/81; 422/82
[58] Field of Search .......... 422/81, 82; 73/53, 61.1 R, 73/61 R; 204/195 B, 195 R, 195 M

[56] References Cited
U.S. PATENT DOCUMENTS

| | | | |
|---|---|---|---|
| 3,098,718 | 7/1963 | Ferrari | 422/82 X |
| 3,165,693 | 1/1965 | Isreeli et al. | 204/195 R UX |
| 3,211,645 | 10/1965 | Ferrari | 422/82 X |
| 3,241,923 | 3/1966 | Ferrari | 422/82 |
| 4,108,602 | 8/1978 | Hanson et al. | 422/81 X |
| 4,219,530 | 8/1980 | Kopp et al. | 422/81 X |

Primary Examiner—G. L. Kaplan

[57] ABSTRACT

A system for analyzing a biological fluid specimen or the like includes an analysis chamber and an electrochemical electrode measuring system connected in sensing relation to the analysis chamber. A flow network connects a sample inlet port and an auxiliary fluid reservoir to the analysis chamber. The flow network includes a sample line connected between the sample inlet port and the analysis chamber and an auxiliary manifold connected to the auxiliary fluid reservoir. A positive displacement pump is connected in the sample line between the analysis chamber and a waste outlet port. A valved T-connection is provided between the sample line and the manifold; an inlet isolation valve is in the sample flow path between the sample inlet and the valved T-connection; an analysis chamber isolation valve is in the sample flow path between the valved T-connection and the analysis chamber; and both the sample line and the manifold have a vent valve, the sample line vent valve being connected between the inlet and chamber isolation valves and the manifold vent valve being connected upstream of the auxiliary fluid reservoir. Coordinated operation of the several valves permits the pump to selectively flow fluid from the auxiliary reservoir or a sample through the analysis chamber, together with imposition of nonlaminar flow conditions by concurrent operation of the vent valves to provide effective cleaning of flow surfaces and analysis chambers.

28 Claims, 16 Drawing Figures

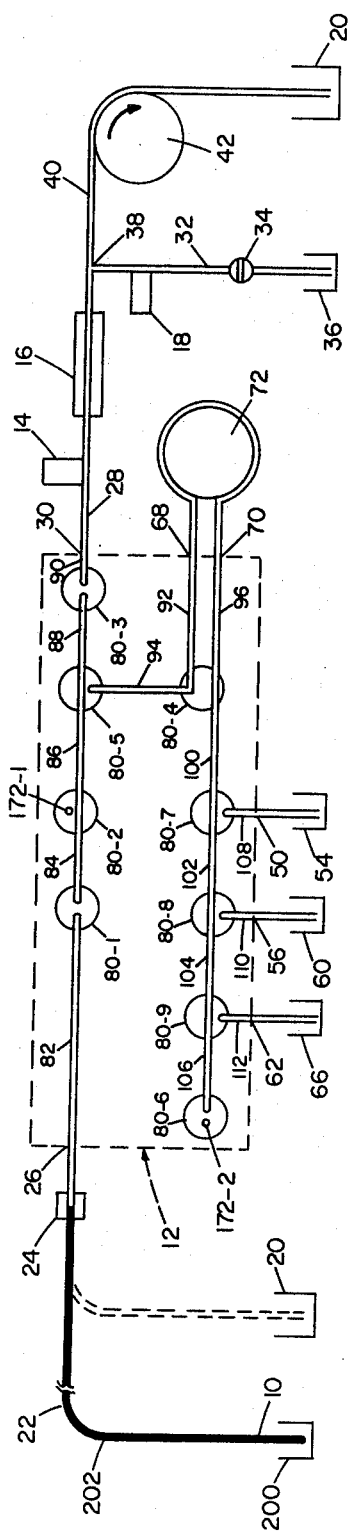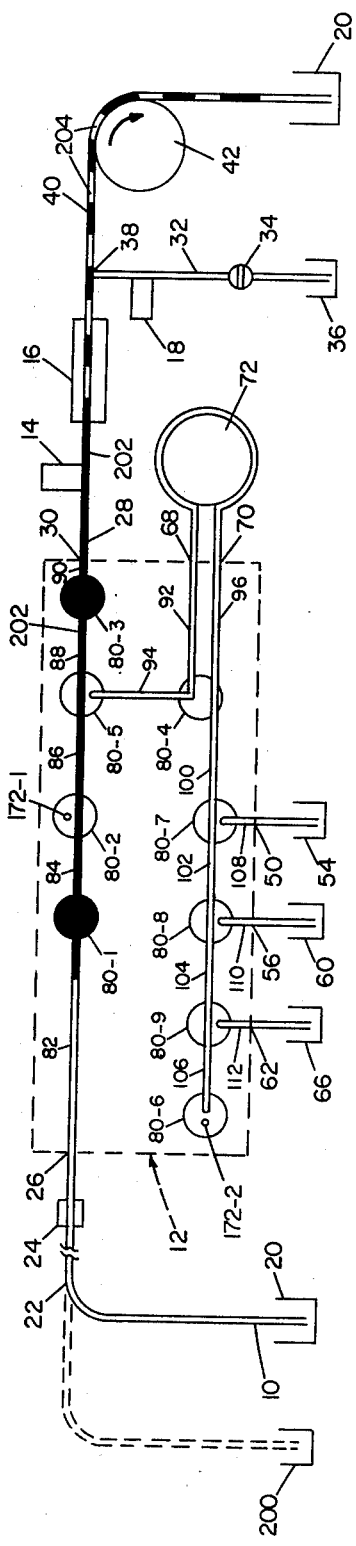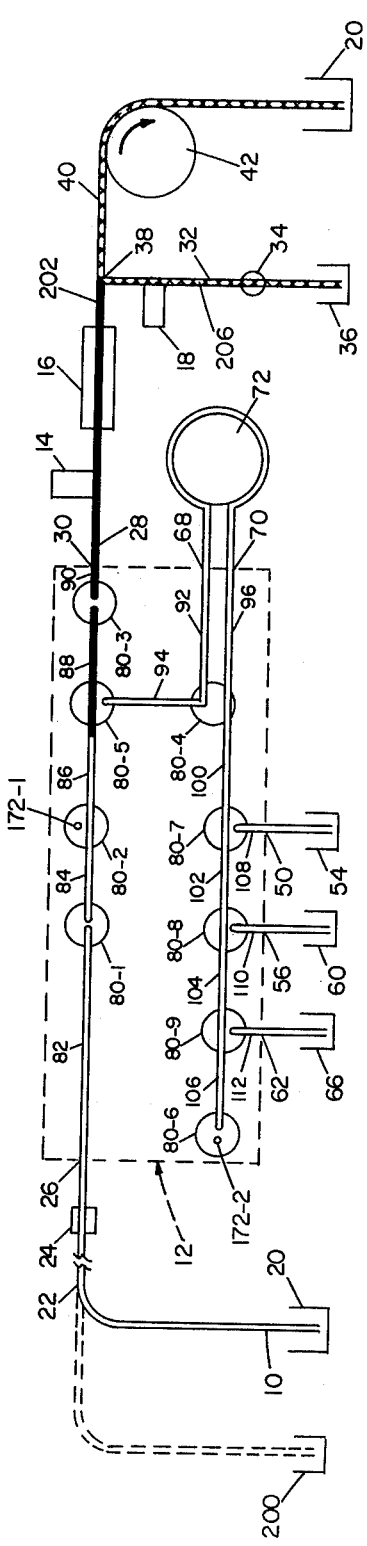

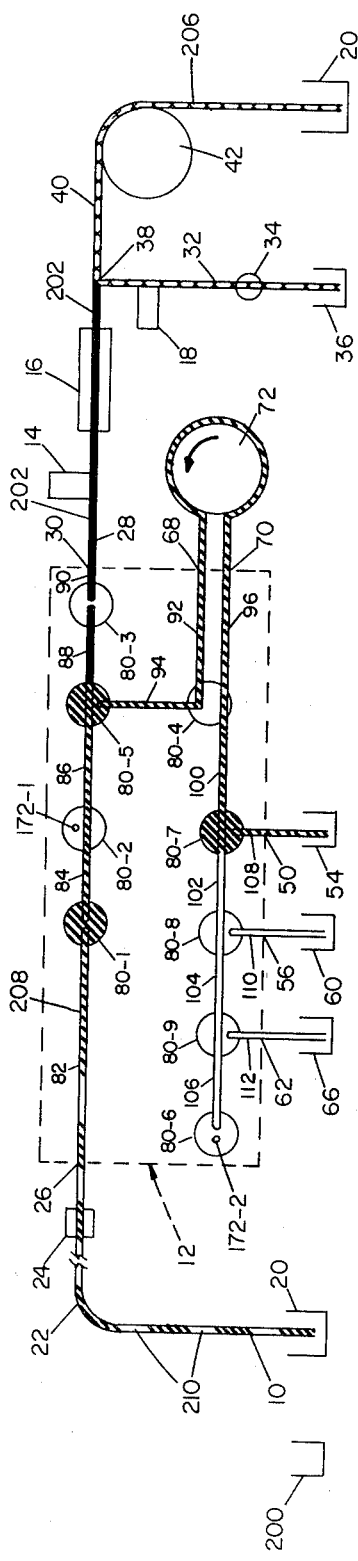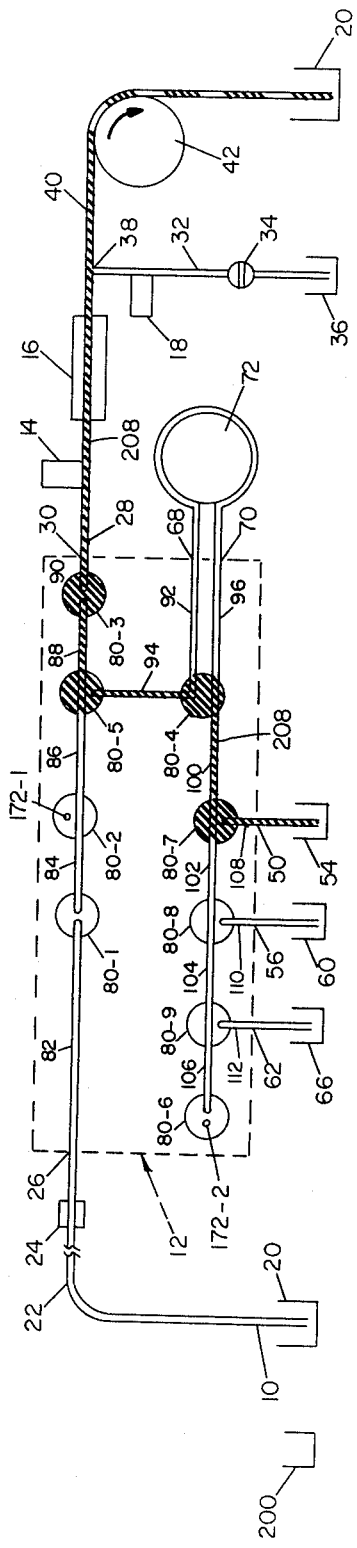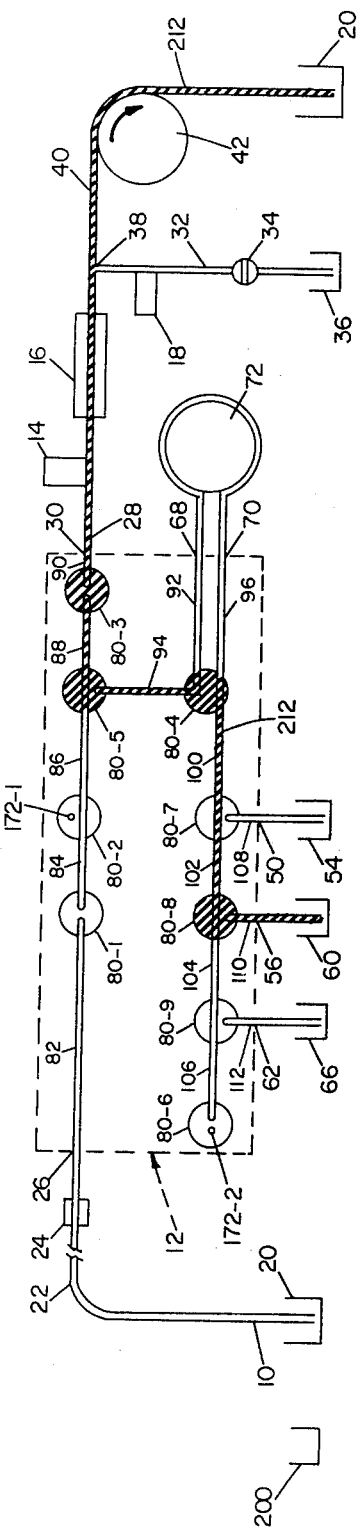

ANALYSIS SYSTEM

This invention relates to apparatus for the analysis of fluid samples and has particular application to apparatus for the analysis of constituents of precious fluids such as blood.

It is frequently desired to obtain an accurate measurement of one or more constituents of a fluid sample of small volume. For example, the values of particular constituents of a blood sample (whole blood, blood serum or plasma) may be useful in providing diagnostic information on metabolic disturbances, assisting in the control of life support devices and in evaluating the effectiveness of therapeutic measures. Analysis systems employing electrochemical electrodes have been developed for such purposes. Such electrochemical electrode systems are used for measurement of concentration of ions of hydrogen, sodium, potassium, and the like. In such systems, the sample to be analyzed is drawn or injected into an analysis chamber for exposure to an ion selective membrane (of glass or plastic material, for example). The magnitude of the electrical potential developed at the sample-membrane interface is related to the ionic concentration of the constituent of interest in the sample solution being analyzed. Both the analysis chamber and sample flow surfaces must be adequately cleaned between sample analysis runs so that there is no cross-contamination or other interaction between successive samples or between samples and calibration fluids, as residue of calibration fluids may have adverse effect on the accuracy of the measurements of the precious fluids.

In accordance with the invention, there is provided a system for analyzing a precious fluid specimen or the like which includes an analysis chamber and an electrochemical electrode measuring system connected in sensing relation to the analysis chamber. A flow network connects a sample inlet port and an auxiliary fluid reservoir to the analysis chamber. The flow network includes a sample line connected between the sample inlet port and the analysis chamber and an auxiliary manifold connected to the auxiliary fluid reservoir. A positive displacement pump is connected in the sample line between the analysis chamber and a waste outlet port. A valved T-connection is provided between the sample line and the manifold; an inlet isolation valve is in the sample flow path between the sample inlet and the valved T-connection; an analysis chamber isolation valve is in the sample flow path between the valved T-connection and the analysis chamber; and both the sample line and the manifold have a vent valve, the sample line vent valve being connected between the inlet and chamber isolation valves and the manifold vent valve being connected upstream of the auxiliary fluid reservoir. Coordinated operation of the several valves permits the pump to selectively flow fluid from the auxiliary reservoir or a sample through the analysis chamber, together with imposition of nonlaminar flow conditions by concurrent operation of the vent valves to provide effective cleaning of flow surfaces and analysis chambers.

In preferred embodiments, the valves are in an array that includes a face plate member with a firm and stable support surface, and a flexible sheet member with a relatively soft and compliant surface that is clamped in conforming and mating engagement with the firm and stable surface of the face plate member by a spring loaded backing plate which maintains consistent clamping and sealing forces. A flow network is formed in one of the engaged surfaces with each valve including a land portion that separates adjacent flow channel portions of the flow network. Each valve also includes an actuator which is arranged to flex the sheet member between a first position in which the surface of the valve sheet member is in mating and sealing engagement with the surface of the face plate member so that the valve land portion sealingly blocks flow between the adjacent channel portions, and a second position in which the sheet surface is spaced from the first position and allows liquid flow across the land surface between the adjacent channel portions. Each valve has a small volume (less than ten microliters) when open and essentially zero deadspace when closed. The gentle and smooth closing action of the valve membrane is in a radially inward direction. Flow transitions imposed by rapid cycling of the valve provide effective cleaning action. The valves provide excellent isolation between different liquids which are handled by the system, in a particular embodiment, successive samples, calibration liquids and conditioning liquids. The valved T-connection in that embodiment has a straight through sample flow path and a valve land that separates the outlet end of the manifold from the sample flow path such that the sample flow path is never closed.

In a particular embodiment, the valve face plate member is transparent and the sample flow path is in the form of a groove that extends along the surface of that member that is engaged by the valve sheet. The valve sheet is opaque and of contrasting color to the fluids (whole blood, blood serum, and plasma) that are to be analyzed. Each valve actuator flexes the sheet in a direction perpendicular to the rigid surface of the face plate to open its valve so that a chamber of generally frusto-conical configuration is formed which is filled with the sample, providing immediate visual indication of the position of the valve, as well as the location of the sample within the flow network.

In that particular embodiment, each valve actuator has a cylindrical head portion embedded in a relatively soft polyurethane membrane sheet, and the flow network includes a channel array formed in the transparent face plate of acrylic plastic. The auxiliary manifold has a plurality of auxiliary liquid reservoirs connected to it, each through one of the valves in the valve array. Disposed in series in the sample flow path downstream from the valve array are two analysis chambers, each of which has an electrochemical electrode associated with it and each electrode has an ion selective membrane exposed at a surface of the sample flow path. Also in the sample flow path, downstream from the analysis chambers, is a fluid junction to which a reference electrode may be connected by an electrolyte salt bridge.

The system permits efficient and accurate analysis of blood and serum specimens of less than 200 microliters volume each.

Other features and advantages of the invention will be seen as the following description of a particular embodiment progresses, in conjunction with the drawings, in which:

FIGS. 11–16 are diagrams showing operational sequences of the instrument shown in FIG. 1.

DESCRIPTION OF PARTICULAR EMBODIMENT

Figure 1:
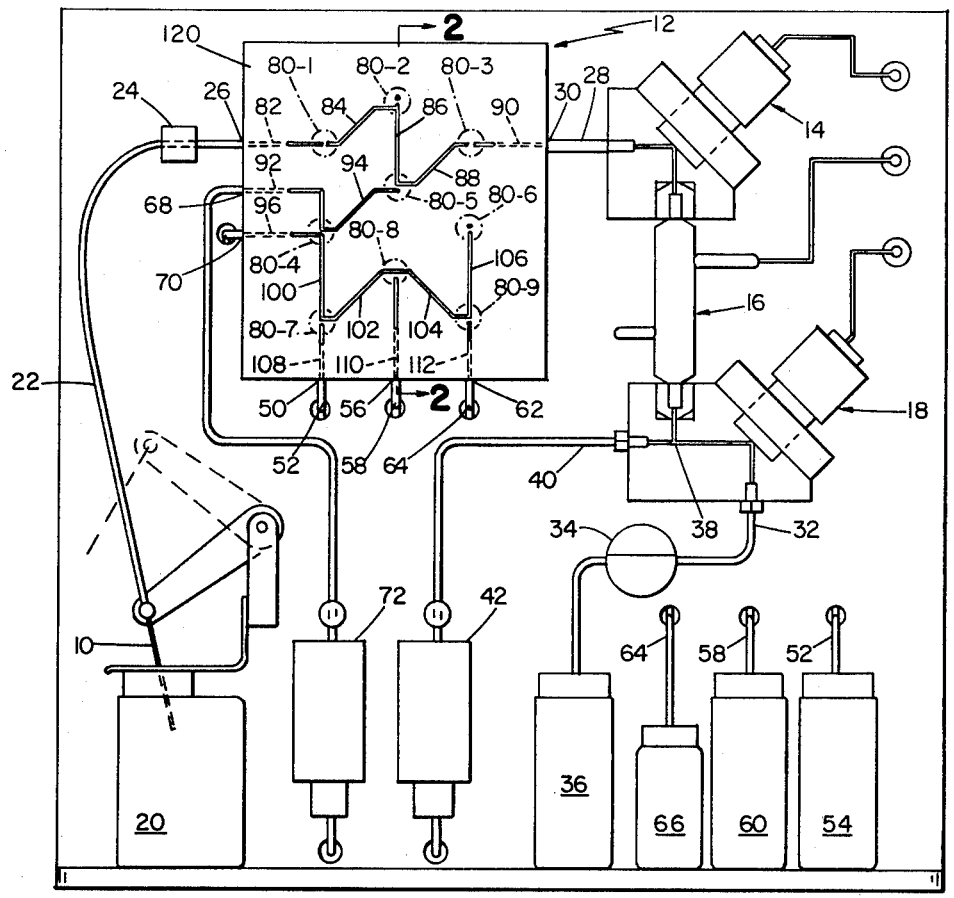
FIG. 1 is a front view of a blood analysis instrument in accordance with the invention.

Shown in FIG. 1 is a front view of a blood analysis instrument that includes a sample probe 10, a valve array 12, a potassium sensing electrode 14, a sodium sensing electrode 16, and a reference electrode 18. Sample probe 10 is movable between a waste receptacle 20 and a sample source. Inlet line 22 is connected between sample probe 10 and inlet 26 of the valve array. Rigid tube 28 is connected between valve array outlet 30 and the potassium sensing electrode 14. Connected to reference electrode 18 through line 32 and pinch valve 34 is a source 36 of reference electrolyte. Line 40 from reference electrode assembly 18 is connected through peristaltic pump 42 to waste receptacle 20.

Valve array 12 also has an inlet 50 connected via line 52 to a first source 54 of calibrating fluid: an inlet 56 connected via line 58 to a second source 60 of calibrating fluid; a third inlet 62 connected via line 64 to a source 66 of conditioner for the sodium electrode 16; and ports 68, 70 connected to peristaltic pump 72.

The valve array 12 includes nine valves 80 and an array of interconnecting passages; passage 82 extending from port 26 to valve 80-1; passage 84 extending from valve 80-1 to valve 80-2; passage 86 extending from valve 80-2 to valve 80-5; passage 88 extending from valve 80-5 to valve 80-3; passage 90 extending from valve 80-3 to outlet port 30; passage 92 extending from port 68 to valve 80-4; passage 94 extending from valve 80-4 to valve 80-5; passage 96 extending from valve 80-4 to port 70; passage 100 extending from valve 80-4 to valve 80-7; passage 102 extending from valve 80-7 to valve 80-8; passage 104 extending from valve 80-8 to valve 80-9; passage 106 extending from valve 80-9 to valve 80-6; passage 108 extending from valve 80-7 to port 50; passage 110 extending from valve 80-8 to port 56; and passage 112 extending from valve 80-9 to port 62.

Figure 2:
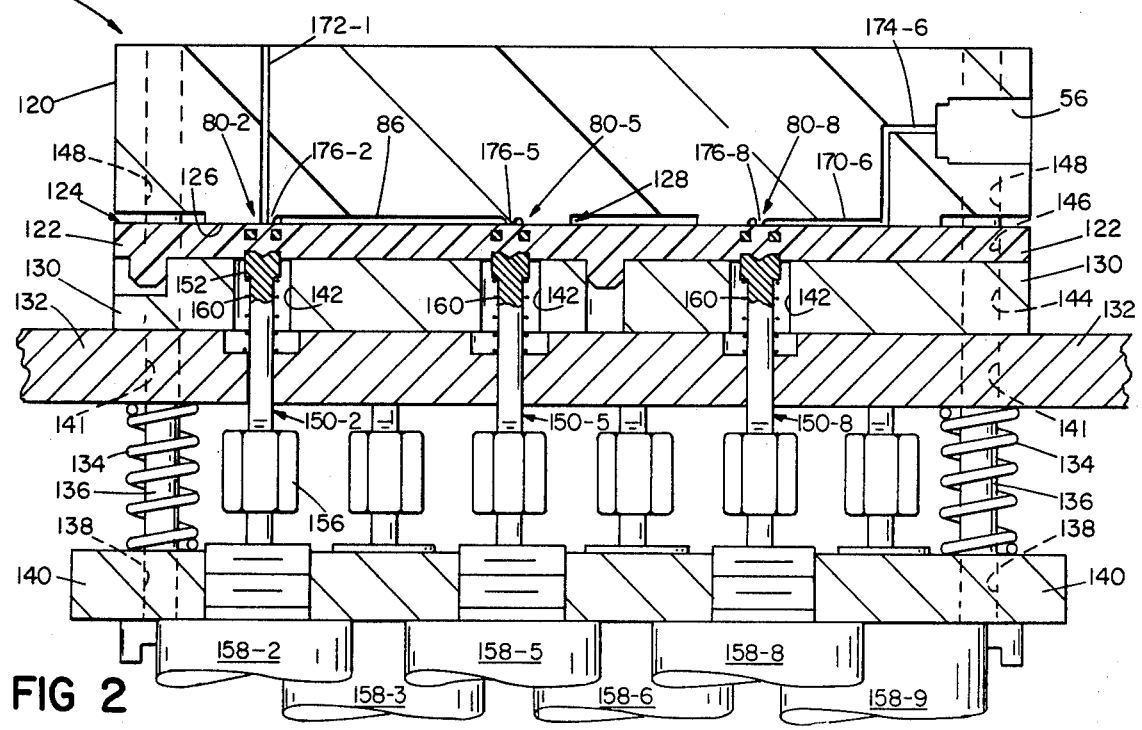
FIG. 2 is a sectional view, taken along the line 2—2, of the valve array employed in the instrument shown in FIG. 1.
Figure 3:
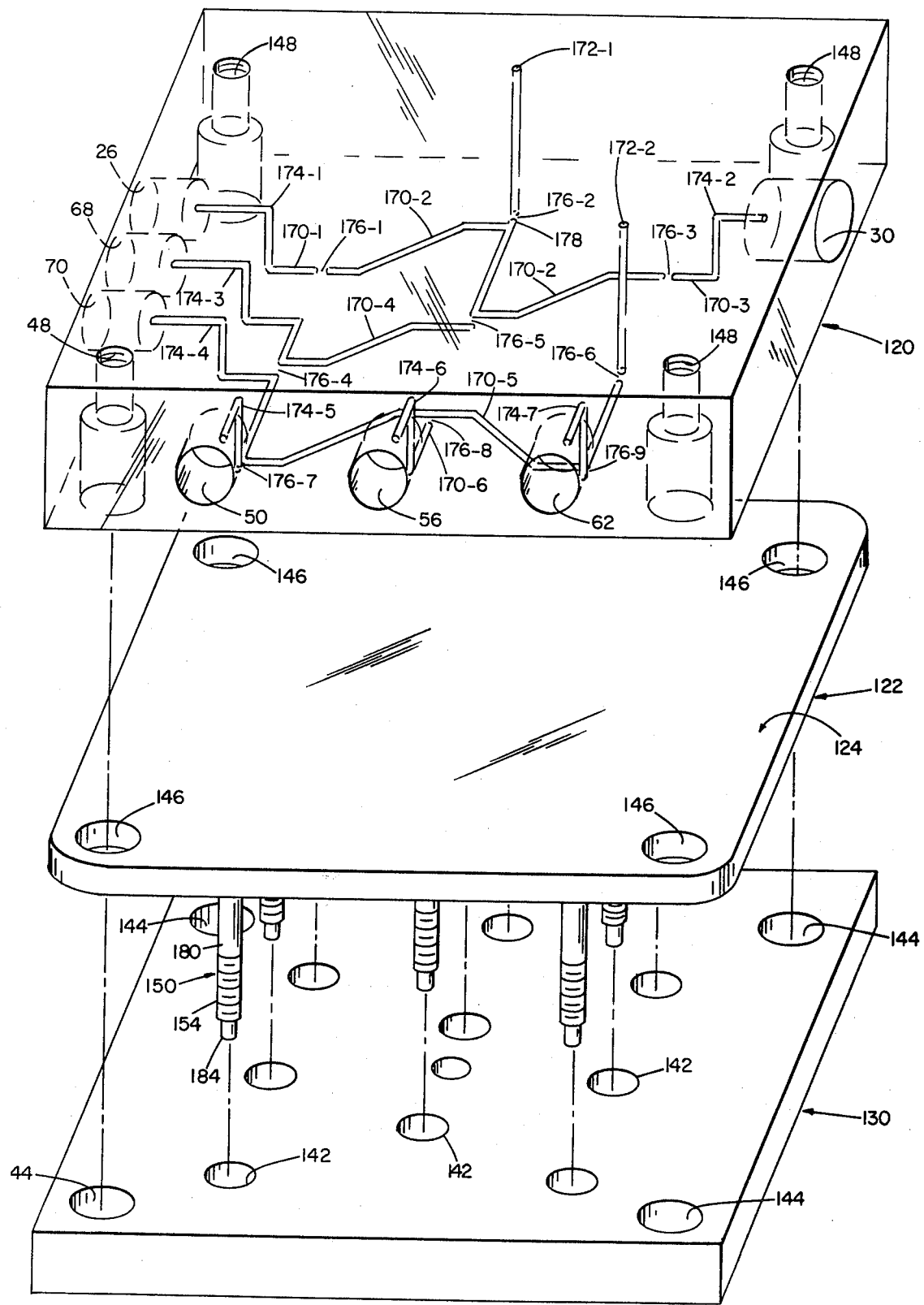
FIG. 3 is an exploded view of components of the valve array shown in FIG. 2.

A sectional view of the valve array 12 is shown in FIG. 2. That valve array includes a transparent face plate 120 of cast acrylic resin that has a width of about eight centimeters, a length of about $8\frac{1}{2}$ centimeters, and a depth of about $1\frac{1}{2}$ centimeters. Clamped against the bottom surface of face plate 120 is a manifold diaphragm sheet 122 of white polyurethane of 40 shore A durometer hardness that has a smooth, pit-free surface 124 (the mold surface having a mirror polish) seated against the surface 126 of the raised land array 128 (FIG. 4) on the lower surface of plate 120. Diaphragm sheet 122 has a thickness of about three millimeters and its width and length dimensions are slightly less than the width and length dimensions of face plate 120. Apertured aluminum backing plate 130 has a thickness of about six millimeters and the same width and length dimensions as face plate 120. Mounting plate 132 is biased against the bottom of backing plate 130 by springs 134 which are supported on headed studs 136 that pass through holes 138 in solenoid support plate 140 and then through holes 141 in mounting plate 132, holes 144 in backing plate 130, holes 146 in diaphragm sheet 122 and are secured in threaded bores 148 in face plate 120.

Secured to diaphragm member 122 is an array of nine actuators 150, the head 152 of each being embedded in the polyurethane manifold sheet 122. Each actuator 150 is connected by a threaded section 154 and coupling 156 to a solenoid actuator 158. A spring 160 (of about one pound closing force) is seated between surface 162 of plunger 150 and recess 164 of mounting plate 132.

Figure 4:
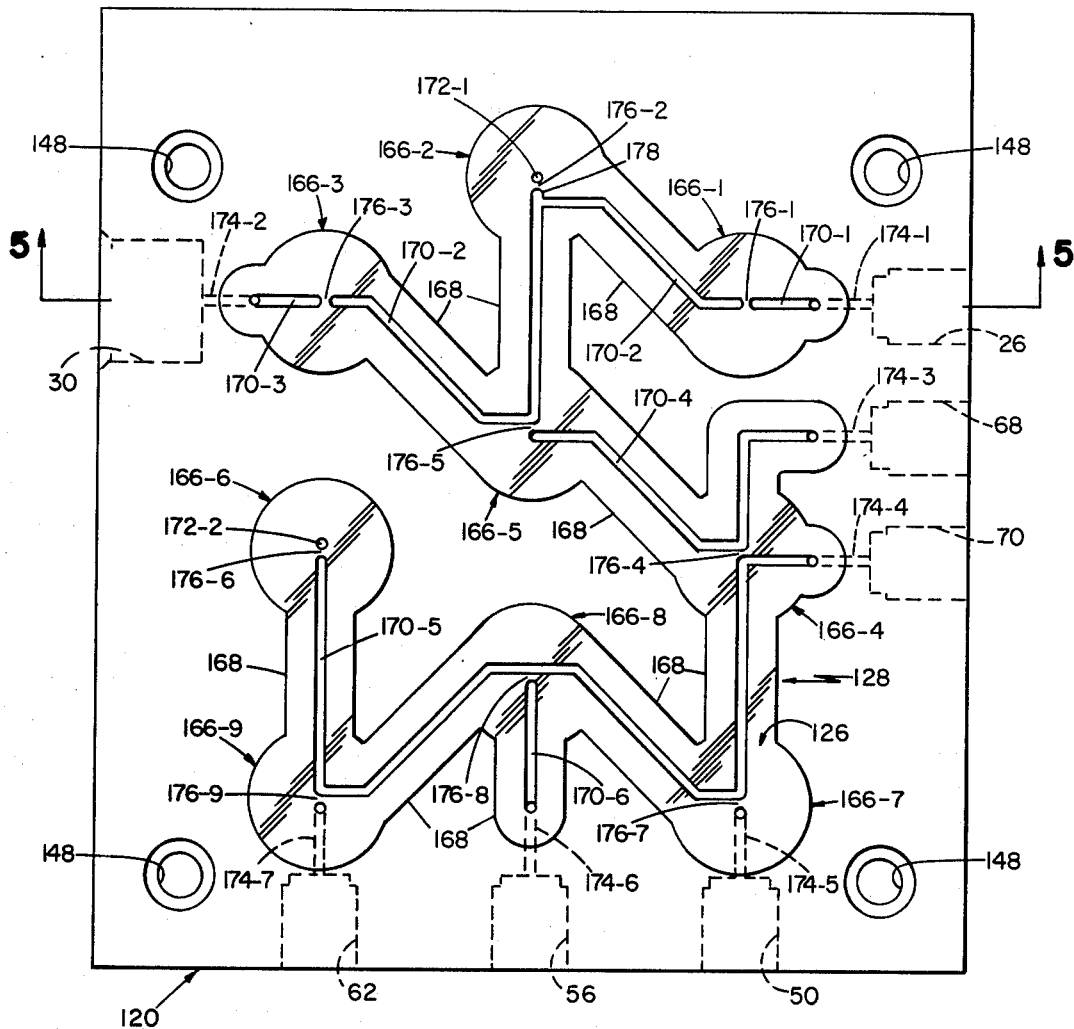
FIG. 4 is an elevational view of the face plate of the valve array showing details of the flow network.
Figure 5:
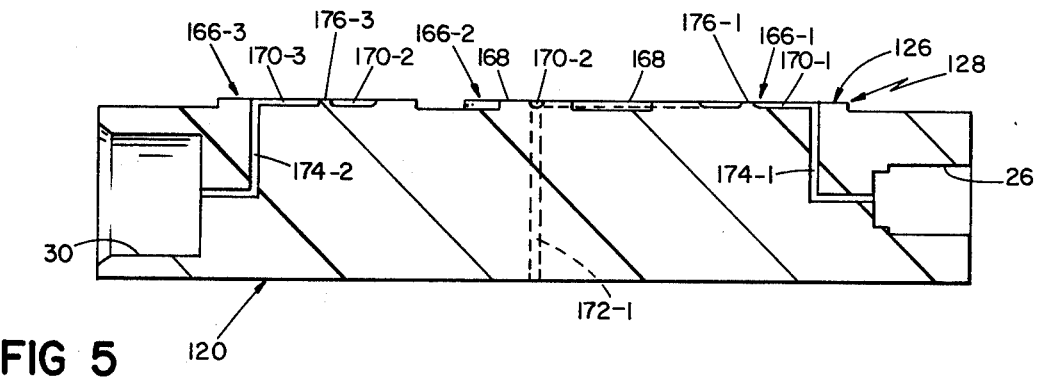
FIG. 5 is a sectional view taken along the line 5—5 of FIG. 4.

Further details of the raised land array 128 in face plate 120 may be seen with reference to FIGS. 4 and 5. Land array 128 includes a set of nine generally circular valve sites 166, each about $1\frac{1}{4}$ centimeter in diameter, and interconnection lands 168, each about $\frac{5}{8}$ centimeter in length. Surface 126 of the land array 128 is about 0.4 millimeter above the base surface of face plate 120 and is flat and smooth (RMS 32). Formed in each valve land and interconnecting land is one or more channels, in the form of grooves or trenches 170 (each about 0.8 millimeter in width and about 0.6 millimeter in depth formed by a ball end mill); through bores 172-1 and 172-2, each about 0.8 millimeter in diameter; and L-shaped passages 174, each of which extends between an external port and a groove in a valve land. Thus, passage 82 extends from port 26 through L-shaped passage 174-1 and groove 170-1 to land 176-1 at valve site 166-1; and groove 170-2 extends from valve site 166-1 through valve sites 166-2 and 166-5 to land 176-3 at valve site 166-3. At each valve site is a valve land 176 about $\frac{1}{4}$ millimeter in width; land 176-1 separating channels 170-1 and 170-2; land 176-2 separating bore 172-1 from stub extension 178 of channel 170-2; land 176-3 separating the end of channel 170-2 from channel 170-3; land 176-5 separating channel 170-2 from channel 170-4; land 176-4 separating channels 170-4 and 170-5; land 176-6 separating channel 170-5 from bore 172-2; land 176-7 separating channel 170-5 from passage 174-5; land 176-8 separating channel 170-5 from 170-6; and land 176-9 separating channel 170-5 from passage 174-7.

Figure 6:
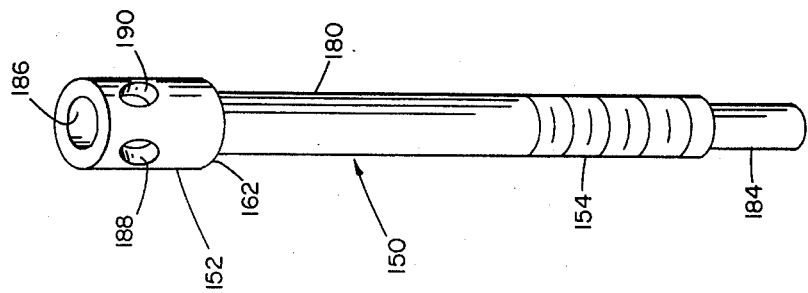
FIG. 6 is a perspective view of a valve actuator rod.

Further details of the valve actuator rod 150 may be seen with reference to FIG. 6. Each rod has a head portion 152 about three millimeters in diameter and about four millimeters in length, a shaft section 180 about two millimeters in diameter with a threaded section 154 about six millimeters in length and a foot portion 184. Formed in head portion 152 is an axially extending bore 186 about $1\frac{3}{4}$ millimeter in diameter and $2\frac{1}{2}$ millimeters deep; and two transverse bores 188, 190 that extend through head 152 and each is about one millimeter in diameter. The heads 152 of actuator 150 are embedded in the manifold diaphragm 122 during the molding operation with polyurethane flowing through bores 186, 188, and 190 to securely affix the actuator head 152 to the diaphragm sheet 122.

Figure 9:
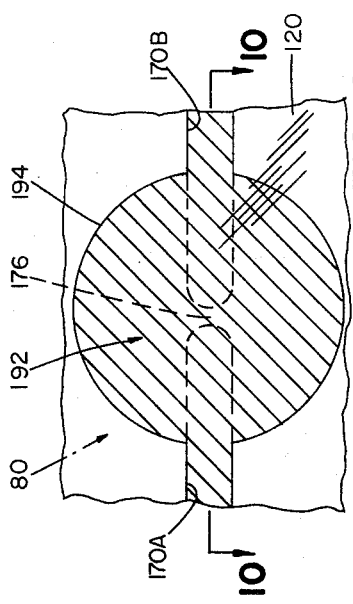
FIG. 9 is a view of the valve of FIG. 7 in open position.
Figure 10:
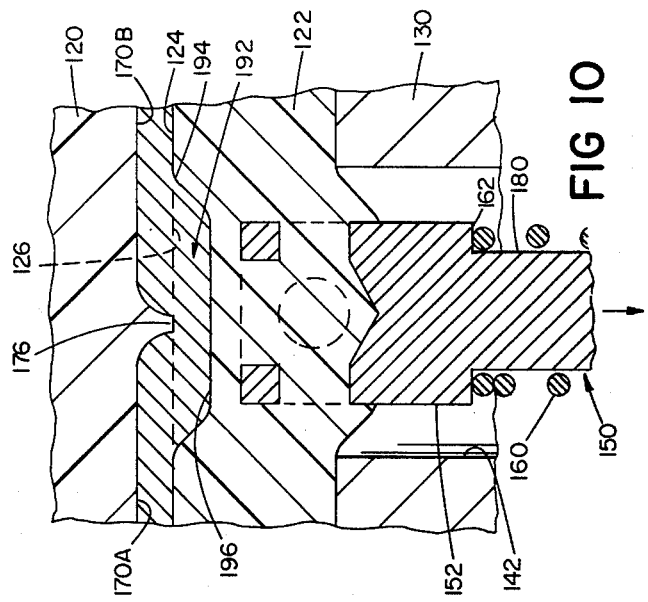
FIG. 10 is a sectional view taken along the line 10—10 of FIG. 9.
Figure 7:
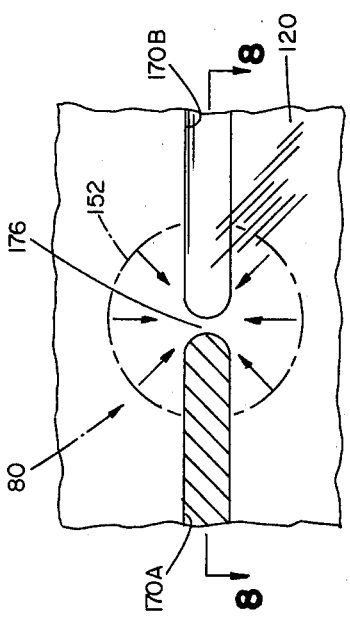
FIG. 7 is a view of a valve in accordance with the invention in closed position.
Figure 8:
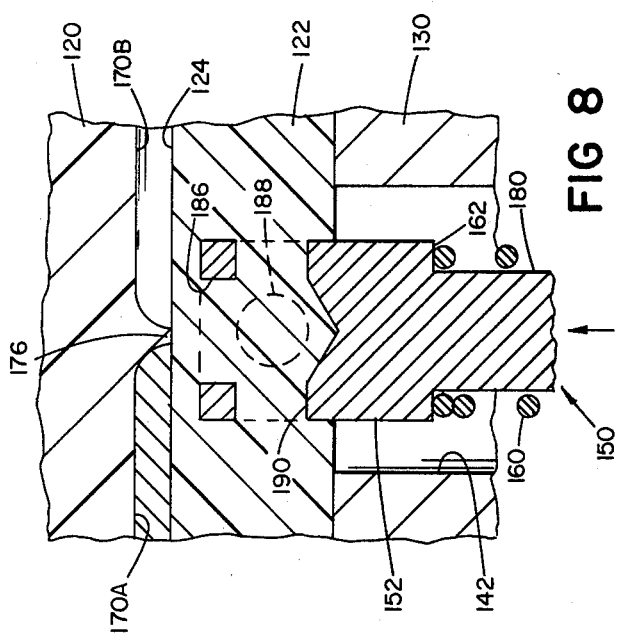
FIG. 8 is a sectional view taken along the line 8—8 of FIG. 7.

Shown in FIGS. 7 and 8 is a view of a valve 80 in closed position with diaphragm surface 124 seated on land 176. The inlet channel 170A is filled with blood (which is visible through transparent face plate 120) but flow to the outlet channel 170B is blocked by the firm seating of diaphragm surface 124 against land 176, in a "zero deadspace" valving action. Movement of actuator 150 by its solenoid 158 (an axial travel of about ¾ millimeter) moves the valve to its fully open position as shown in FIGS. 9 and 10. In that position, a valve chamber 192 of frustoconical configuration is formed over land 176 with a circular peripheral margin 194 in contact with plate surface 126, and a generally flat surface 196 spaced from land 176. The blood from channel 170A flows through chamber 192 to outlet channel 170B, and the fluid color contrast with the white background of diaphragm 122 (a circular area about four millimeters in diameter) provides an indication that is clearly visible through the transparent face plate 120 of the open position of the valve.

When actuator 150 is released, the membrane resilience supplemented by a gentle closing force of spring 160 returns the flexed portion of diaphragm 122 to its initial seated position in a smooth, radial inward, wiping action which flows fluid from the valve chamber 102 into the channels 170A and 170B so that the diaphragm surface 124 gently seats on the plate surface 126 with essentially no damage to delicate cellular material in the fluid being controlled by the valve.

Isolation valves 80-1 and 80-3 are of the type shown in FIGS. 7-10; T-valves 80-5, 80-7, 80-8, and 80-9 have a straight through channel that is always open and a second channel separated from the straight through channel by a valve land; vent valves 80-2 and 80-6 have a channel separated from a perpendicular vent passage via a valve land; and shunt valve 80-4 has two flow through channels separated by a valve land.

An operational sequence of the instrument is indicated in the diagrams of FIGS. 11–16. With the tip of sample probe 10 immersed in a sample of the liquid to be analyzed in container 200, as indicated in FIG. 11, valves 80-1 and 80-3 are opened by their respective solenoids 158-1 and 158-3, and peristaltic pump 42 is operated to inspirate sample 202 through probe 10 to sensor 24. When sensor 24 signals that the desired quantity of sample to be analyzed (about 180 microliter volume of blood or serum) valve 80-1 is closed and valve 80-2 is opened to vent the line between valve 80-1 and pump 42. Pump 42 is then stopped and the sample 202 to be analyzed thus is stored in line 22 as indicated in FIG. 11.

When probe 10 has been wiped and inserted into waste receptacle 20, vent valve 80-2 is closed and probe isolation valve 80-1 is opened, and pump 42 is again energized to draw the sample 202 through the valve array 12 into the sample chambers of electrode systems 14 and 16. As the blood sample 202 is being drawn past valve 80-2, that valve is pulsed seven times, the valve being open for about 40 milliseconds and closed for about 130 milliseconds at each pulse cycle, so that seven segments 204 of air are inserted into the leading portion of sample 202, as indicated in FIG. 12. This segmenting of the blood sample produces liquid flow transients which clean the surfaces of the flow passages and analysis chambers. This segmented leading portion of the blood sample 202 is drawn through the electrode chambers 14 and 16 and past the reference junction 38 and through line 40. Electrode isolation valve 80-3 is closed on the trailing portion of the blood sample 202 as indicated in FIG. 13, so that the blood sample is held in the analysis chambers of potassium electrode 14 and sodium electrode 16. Pinch valve 34 is simultaneously opened and electrolyte 206 is drawn from reservoir 36 past reference electrode 18 and through junction 38 to form a conductive path from reference electrode 18 to the blood sample 202 as indicated in FIG. 13. About one second after valve 34 is opened, pump 42 is stopped and the electrodes 14, 16 are allowed to equilibrate with the sample 202.

During that equlibration interval, probe 10 is back flushed by means of pump 72. Valves 80-1, 80-5, and 80-6 are opened. With valve 80-4 closed, pump 72 is operated and the manifold line (sections 100, 102, 104, and 106) is dried, the liquid being pumped by pump 72 from the manifold through probe 10 into waste receptacle 20. Calibrant valve 80-7 is then opened and liquid 208 is drawn from reservoir 54 by pump 72 in a back flushing flow through sample probe 10 to waste container 20. During this flush cycle, pulse operation of valve 80-6 introduces segments 210 of air into the leading portion of the flush liquid 208 as indicated in FIG. 14. After the back flush interval, all pumping is stopped for the remainder of the equilibration interval (about eight seconds), and then data is taken from the sodium and potassium electrode systems.

After the data has been taken, the analysis chambers are flushed and a calibration check is run. Valves 80-1 and 80-3 are opened and probe 10 is aspirated dry by pump 42 with concurrent pulsing of valve 80-2 to clean that valve. Valve 80-1 is then closed; valves 80-4, 80-5, and 80-7 are opened; and pump 42 pulls calibrating liquid from reservoir 54 through the sample analysis chambers of electrode systems 14 and 16 as indicated in FIG. 15. This flow of liquid has its leading edge segmented by operation of air valve 80-6 to provide cleaning action of the flow passage surfaces and analysis chambers; and then valve 80-6 is closed so that there is a continuous flow of calibration fluid through the analysis chambers of electrode systems 14 and 16 as indicated in FIG. 15. Valve 80-3 is then closed and valve 34 is opened to create an electrolyte-calibration liquid interface at junctions 38, and the calibration of electrodes 14 and 16 is checked. During the flushing and cleaning cycle of the probe (FIG. 14) and of the analysis chambers (FIG. 15) each valve in the sample flow path (valves 80-1, 80-2, 80-5, and 80-3) is opened and closed in a flutter action which provides effective cleaning of the valve chambers 192. Thus the valves, probe 10, and the analysis chambers of the electrode systems 14 and 16 are cleaned in preparation for the next analysis cycle.

Calibration fluid from reservoir 60 or conditioning fluid from reservoir 66 may similarly be pumped through the analysis chambers of electrode systems 14 and 16. As indicated in FIG. 16, for example, by opening valve 80-8 rather than valve 80-7, calibration liquid 212 is pumped from the reservoir 60, the closed valve 80-7 providing complete isolation of calibration liquid 206. In operation, manifold vent valve 80-6 is first opened together with valves 80-4, 80-5 and 80-7, and pump 42 clears (dries) the entire manifold line (sections 94, 100, 102, 104 and 106). Valve 80-6 is then closed and valve 80-7 is opened so that liquid is pumped from reservoir 60 through the analysis chambers as indicated in FIG. 16. The flow of each such liquid may be segmented with air by operation of valve 80-6, as desired.

The analysis system provides efficient handling of small volumes of specimens to be analyzed. A blood or serum specimen of less than 200 microliters volume is analyzed while the volume of a urine specimen is about 700 microliters. Cross-contamination is minimized by the valve configurations, the manifold arrangement and the valve interconnections. Each liquid line can be pumped dry so that there is no liquid-liquid interface, and each has a valved vent to atmosphere. Each valve is easily cleaned and has low (essentially zero) residual volume.

While a particular embodiment of the invention has been shown and described, various modifications will be apparent to those skilled in the art, and therefore it is not intended that the invention be limited to the disclosed embodiment or to details thereof and departures may be made therefrom within the spirit and scope of the invention.

What is claimed is:

1. A system for analyzing a biological fluid or the like comprising
    an analysis chamber, a measuring system connected in sensing relation to said analysis chamber,
    a flow network for connecting a sample inlet port and an auxiliary fluid reservoir to said analysis chamber, and a pump connected between said analysis chamber and an outlet port, said flow network including
    a sample flow path connected between said sample inlet port and said analysis chamber,
    an auxiliary fluid manifold for connection to said auxiliary fluid reservoir,
    a valved T-connection between said sample flow path and said manifold,
    an inlet isolation valve in said sample flow path between said sample inlet and said valved T-connection,
    a chamber isolation valve in said sample flow path between said valved T-connection and said analysis chamber,
    a sample line vent valve between said inlet and chamber isolation valves, and
    a manifold vent valve connected to said manifold.

2. The system of claim 1 and further including an auxiliary fluid isolation valve connected between said manifold and said auxiliary fluid reservoir for controlling flow of fluid from said reservoir to said manifold.

3. The system of claim 1 and further including a valve control arrangement for controlling said valves to provide
    a first (sample intake) mode in which said sample flow path is in fluid communication with said sample inlet port so that fluid from a sample to be analyzed may be flowed into said sample flow path,
    a second (analysis) mode in which said sample flow path is in fluid communication with said analysis chamber so that a fluid sample in said sample flow path may be flowed into said analysis chamber,
    a third (inlet flush) mode in which said manifold is in fluid communication with said sample port, and
    a fourth (analysis chamber flush) mode in which said manifold is in fluid communication with said analysis chamber.

4. The system of claim 1 wherein said pump is a positive displacement pump, and further including a second positive displacement pump for pumping fluid through said manifold to said valved T-connection.

5. The system of claim 1 wherein said measuring system includes an electrochemical electrode with an ion selective membrane that is arranged for exposure to sample in said sample flow path.

6. The system of claim 1 wherein said measuring system includes a reference electrode, a supply of electrolyte, and an electrolyte conduit connected to form a fluid junction with said sample flow path between said electrolyte reservoir and said pump.

7. The system of claim 1 wherein said manifold vent valve is at the end of said manifold remote from said valved T-connection.

8. A fluid analysis system comprising
    an analysis chamber, a measuring system connected in sensing relation to said analysis chamber,
    a flow network for connecting a sample inlet port and a plurality of auxiliary fluid reservoirs to said analysis chamber, and a pump connected between said analysis chamber and an outlet port, said flow network including
    a sample flow path connected between said sample inlet port and said analysis chamber,
    an auxiliary fluid manifold for connection to said auxiliary fluid reservoir,
    a valved T-connection between said sample flow path and said manifold,
    an auxiliary fluid reservoir isolation valve between each said reservoir and said manifold, and
    a manifold vent valve connected at the end of said manifold remote from said valved T-connection.

9. The system of claim 8 and further including means for pulsing said vent valve for introducing segments of gas into liquid in said flow network.

10. The system of claim 8 and further including a further vent valve in said sample flow path between said inlet isolation valve and said valved T-connection.

11. The system of either claim 1 or 8 wherein said valves are in an array that includes
    a face plate member that has a rigid surface,
    a flexible valve sheet member that has a surface that is softer and more resilient than said face plate surface for mating engagement with said face plate surface,
    a network of channel portions in one of said members with a plurality of valve land portions, each said valve land portion being located between two adjacent ones of said channel portions, the surfaces of said land portions being coincident with the surface of the member in which they are located,
    and a valve control arrangement that includes a plurality of valve actuators, each said actuator being arranged to flex said sheet member between a first position in which said valve sheet surface is in mating and sealing engagement with said valve face plate surface to sealingly block flow between adjacent ones of said channel portions, and a second position in which said sheet surface is spaced away from said first position to allow flow between said adjacent channel portions across the land portion corresponding to that actuator.

12. The system of claim 11 wherein said channel portions are in the surface of the member in which said land portion is located.

13. The system of claim 11 wherein said face plate member is transparent.

14. The system of claim 11 wherein each said actuator moves said sheet perpendicular to said rigid surface of said face plate member.

15. The system of claim 11 wherein each said actuator has a portion embedded in said sheet member.

16. The system of claim 11 wherein each said actuator has a cylindrical head embedded in said sheet member effective to stabilize the surface of said sheet member in the immediate vicinity of each said land portion.

17. The system of claim 11 wherein said flexible sheet member is opaque and said face plate member is transparent.

18. The system of claim 11 wherein each said actuator includes biasing means that acts to urge said sheet member into mating engagement with the surface of said face plate member.

19. The system of claim 11 wherein the surfaces of said face plate member and said sheet member are planar.

20. The system of claim 11 and further including backing plate structure and biasing means from resiliently clamping said sheet member between said face plate member and said backing plate structure.

21. The system of claim 20 wherein said backing plate structure has a plurality of circular openings in which said actuators are disposed such that a frustoconical valve chamber is defined by the marginal surfaces of said circular opening when any one of said actuators flexes said sheet member away from said face plate member.

22. The system of claim 20 wherein said measuring system includes an electrochemical electrode with an ion selective membrane that is arranged for exposure to sample in said sample flow path, a reference electrode, a supply of electrolyte, and an electrolyte conduit connected to form a fluid junction with said sample flow path between said electrolyte reservoir and said pump.

23. The system of claim 22 wherein said face plate member is transparent, said channel portions are in a planar surface of said face plate member, said flexible sheet member is opaque and each said actuator includes biasing means that acts to urge said sheet member into mating engagement with the planar surface of said face plate member.

24. The system of claim 23 and further including a valve control arrangement for controlling said valves to provide a first (sample intake) mode in which said sample flow path is in fluid communication with said sample inlet port so that fluid from a sample to be analyzed may be flowed by operation of said pump into said sample flow path, a second (analysis) mode in which said sample flow path is in fluid communication with said analysis chamber so that a fluid sample in said sample flow path may be flowed by operation of said pump into said analysis chamber, a third (inlet flush) mode in which said manifold is in fluid communication with said sample inlet port through said valved T-connection, and a fourth (analysis chamber flush) mode in which said manifold is in fluid communication with said analysis chamber through said valved T-connection.

25. The system of claim 11 wherein said channel portions include a groove that extends along the surface of said face plate member.

26. The system of claim 11 wherein each said isolation valve includes two grooves that extend along the surface of the member in which said land portion is located, and said land portion is located between said two grooves.

27. The system of claim 11 wherein said valved T-connection includes a flow through groove that extends along the surface of said face plate member and forms a portion of said sample flow path, and a land portion is between said groove and the end of said manifold so that said flow through groove is isolated from said manifold when said valve sheet surface is in mating and sealing engagement with said face plate surface, and fluid is permitted to flow between said manifold and said groove across said land portion when said sheet surface is spaced away from said valve body surface.

28. The system of claim 11 wherein said vent valve includes a flow through groove that extends along the surface of said face plate member and forms a portion of said sample flow path, a vent passage that extends from a port in the surface of said face plate member in which said land portion is located to the atmosphere, and a land portion is between said groove and said port so that said flow through groove is isolated from said port when said valve sheet surface is in mating and sealing engagement with said face plate surface, and air is permitted to flow between said port and said flow through groove across said land portion when said sheet surface is spaced away from said valve body surface.

* * * * *